(12) United States Patent
Bhargava

(10) Patent No.: US 12,245,957 B1
(45) Date of Patent: Mar. 11, 2025

(54) PROSTHETIC

(71) Applicant: Arav Yash Bhargava, McLean, VA (US)

(72) Inventor: Arav Yash Bhargava, McLean, VA (US)

( * ) Notice: Subject to any disclaimer, the term of this patent is extended or adjusted under 35 U.S.C. 154(b) by 0 days.

(21) Appl. No.: 18/781,531

(22) Filed: Jul. 23, 2024

(51) Int. Cl.
*A61F 2/78* (2006.01)
*A61F 2/54* (2006.01)

(52) U.S. Cl.
CPC .......... *A61F 2/78* (2013.01); *A61F 2002/543* (2013.01)

(58) Field of Classification Search
CPC .............................. A61F 2/78; A61F 2002/543
See application file for complete search history.

(56) References Cited

U.S. PATENT DOCUMENTS

| | | | |
|---|---|---|---|
| 8,414,658 B2 | 4/2013 | Johnson et al. | |
| 9,283,093 B2 | 3/2016 | Alley | |
| 9,468,543 B2 | 10/2016 | Hurley et al. | |
| 10,172,724 B2 | 1/2019 | Thomas | |
| 11,596,219 B2 | 3/2023 | Alley | |
| 11,617,667 B2 | 4/2023 | Will et al. | |
| 11,801,154 B2 | 10/2023 | Bache et al. | |
| 2011/0071647 A1* | 3/2011 | Mahon | A61F 2/80 623/33 |
| 2015/0230945 A1* | 8/2015 | Bache | A61F 2/7812 623/33 |
| 2020/0297514 A1 | 9/2020 | Prescott et al. | |
| 2023/0121736 A1 | 4/2023 | Gair, Jr. | |
| 2023/0255803 A1* | 8/2023 | Kuniholm | A61F 2/5046 623/57 |

FOREIGN PATENT DOCUMENTS

| | | |
|---|---|---|
| CN | 103655011 B | 4/2016 |
| CN | 111803251 B | 2/2023 |
| CN | 113855348 B | 1/2024 |

OTHER PUBLICATIONS

Baldock, M., et al., "Adjustable prosthetic sockets: a systematic review of industrial and research design characteristics and their justifications", Journal of NeuroEngineering and Rehabilitation, vol. 20, Nov. 6, 2023, 18 pages.

Biddiss, E., et al., "Upper-limb prosthetics: critical factors in device abandonment", Am J Phys Med Rehabil, vol. 86, No. 12, Dec. 2007, pp. 977-987.

(Continued)

*Primary Examiner* — Bruce E Snow

(74) *Attorney, Agent, or Firm* — Boone IP Law

(57) ABSTRACT

A prosthetic for a limb that extends distally to a limb end includes a main body and plural struts. The main body has an opening for receiving the limb end. The main body defines a first zone of coverage of the limb. The struts are coupled to the main body and distributed along the circumference of the main body. Each strut has a main longitudinal extent that is essentially orthogonal to the circumference of the main body and that extends away from the main body to define a second zone of coverage of the limb that is adjacent to the first zone of coverage. Each strut includes a plurality of transverse through-openings configured to receive a lace. The transverse through-openings extend tangentially to the second zone of coverage.

19 Claims, 8 Drawing Sheets

(56) References Cited

OTHER PUBLICATIONS

Cruz, D. M., et al., "Assistive Technology Accessibility and Abandonment: Challenges for Occupational Therapists", The Open Journal of Occupational Therapy, vol. 4, No. 1, Jan. 2016, 9 pages.

Drew, A. J., et al., "Transhumeral loading during advanced upper extremity activities of daily living", Plos One, vol. 12, No. 12, Dec. 19, 2017, 13 pages.

Hallworth, B. W., et al., "A Modular Adjustable Transhumeral Prosthetic Socket for Evaluating Myoelectric Control", IEEE Journal of Translational Engineering in Health and Medicine, vol. 8, Jul. 1, 2020, 10 pages.

Hansen, T. C., et al., "A Multi-User Transradial Functional-Test Socket for Validation of New Myoelectric Prosthetic Control Strategies", Front. Neurorobot., vol. 16, Jun. 17, 2022, 12 pages.

Hanspal, R. S., et al., "Prosthetic socket fit comfort score", Disability and Rehabilitation, vol. 25, No. 22, Jul. 1, 2003, pp. 1278-1280.

Lao, C., et al., "A market landscape and strategic approach to increasing access to prosthetic devices and related services in low- and middle-income countries", ATscale under the AT2030 Programme, Apr. 2020, 56 pages.

Mcdonald, C. L., et al., "Global prevalence of traumatic non-fatal limb amputation", Prosthetics and Orthotics International, vol. 45, vol. 2, Apr. 2021, pp. 105-114.

Miller, L. A., et al., "A novel, low-cost transradial socket fabrication method using mass-producible components and expanding rigid foam", Prosthetics and Orthotics International, vol. 45, No. 1, Feb. 2021, pp. 89-93.

Olsen, J., et al., "3D-Printing and Upper-Limb Prosthetic Sockets: Promises and Pitfalls", IEEE Trans Neural Syst Rehabil Eng., vol. 29, 2021, 9 pages.

Pruzansky, M. E., "Right Arm Normal Anatomy", HandSport Surgery Institute, Oct. 2, 2023.

Rand, S., et al., "Upper Limb Amputations", PM&R KnowledgeNow., available online at: <https://now.aapmr.org/upper-limb-amputations/>, Aug. 26, 2021, 29 pages.

Stelt, M. V., et al., "Strength testing of low-cost 3D-printed transtibial prosthetic socket", Proc Inst Mech Eng H., vol. 236, No. 3, Dec. 1, 2021, pp. 367-375.

Zuniga, J., et al., "Cyborg beast: a low-cost 3d-printed prosthetic hand for children with upper-limb differences", BMC Research Notes, vol. 8, Jan. 20, 2015, 9 pages.

Zuniga, M. Z., et al., "Remote fitting procedures for upper limb 3d printed prostheses", Expert Review of Medical Devices, vol. 16, No. 3, 2019, pp. 257-266.

\* cited by examiner

PROSTHETIC

TECHNICAL FIELD

The present disclosure relates to prosthetics, including, for example, prosthetics configured to accommodate a residual limb, e.g., of users having undergone transradial amputation.

BACKGROUND

As of 2017, there were 57.7 million people with limb amputation worldwide (McDonald et al., 2021). An estimated 40 million of these amputees live in the developing world, where there is a high prevalence of injuries and illnesses and a lack of medical services, resulting in heightened rates of limb loss (Lao et al., 2020).

Of the millions of amputees in the developing world (30% with upper limb loss), only about 5% have access to prosthetic devices (Lao et al., 2020). Without a prosthetic device, these individuals are denied opportunities to succeed. A key reason for this lack of accessibility is that prosthetic research has primarily focused on enhancing prosthetic technology, and as a result, the most common offerings are (1) very expensive (e.g., ranging from $4000-$8000 for body-powered prosthetics); (2) inflexible; (3) hard to produce in volume; (4) easy to damage; and (5) require a healthcare professional to fit and help manage them (Rand et al., 2021; Cruz et al., 2016; Biddiss et al., 2007). For developing countries, where the average income is less than $300 annually, and there is a scarcity of trained prosthetists, conventional prosthetics are not viable solutions. In addition, for children, these issues are compounded because as they grow, their prosthetics are often not size-adjustable—as such, every six months, a new prosthetic device is typically required (Zuniga et al., 2019). Furthermore, without custom-fit, conventional prosthetic sockets can lead to numerous health complications.

Traditional fabrication of prosthetic sockets includes several time-consuming and expensive steps: casting, modification, and lamination (Olsen et al., 2021). With traditional fabrication, amputees must visit frequently and wait for long periods of time (e.g., 2-5 weeks) to receive their socket (Olsen et al., 2021). Additionally, the fabricator of the socket must be a trained prosthetics professional. Access to these professionals is very limited in developing countries.

3D printing, including, e.g., fused deposition modeling (FDM), can provide low-cost, rapid prosthetic fabrication. However, conventional 3D-printed prosthetic sockets often face problems in durability due to the weak interfaces between their layer-by-layer structure (Zuniga et al., 2019). Therefore, identifying the most durable materials, with tested data supporting the results, is critical to its success (van der Stelt et al., 2021).

Several approaches have been used to create upper-limb universal-fit devices, including foam expandable sockets, universal-fit hook-and-loop sockets, and strut-based test sockets (Miller et al., 2021; Hallworth et al., 2020; Hansen et al., 2022). However, these designs have been unsuccessful and expensive because of low load-bearing capabilities, discomfort, and complex fabrication processes.

SUMMARY

A prosthetic is disclosed for a limb extending distally to a limb end. The prosthetic comprises a main body having an opening for receiving the limb end and having a circumference. The main body defines a first zone of coverage of the limb. The prosthetic further comprises a plurality of struts coupled to the main body and distributed along the circumference of the main body. Each strut has a main longitudinal extent that is essentially orthogonal to the circumference of the main body and that extends away from the main body to define a second zone of coverage of the limb that is adjacent to the first zone of coverage. Each strut includes a plurality of transverse through-openings configured to receive a lace. The transverse through-openings extend tangentially to the second zone of coverage.

BRIEF DESCRIPTION OF THE DRAWINGS

Other features and advantages disclosed herein will become more apparent from the following detailed description of exemplary embodiments when read in conjunction with the attached drawings.

DETAILED DESCRIPTION

Figure 1:
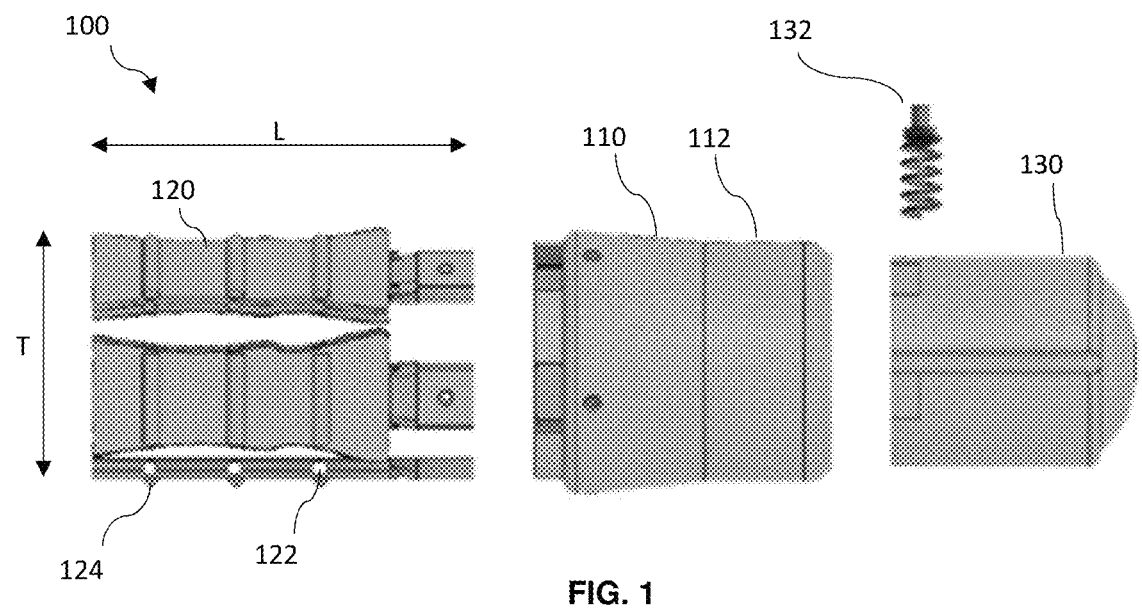
FIG. 1 is a schematic exploded side view of an exemplary embodiment of a prosthetic.
Figure 2:
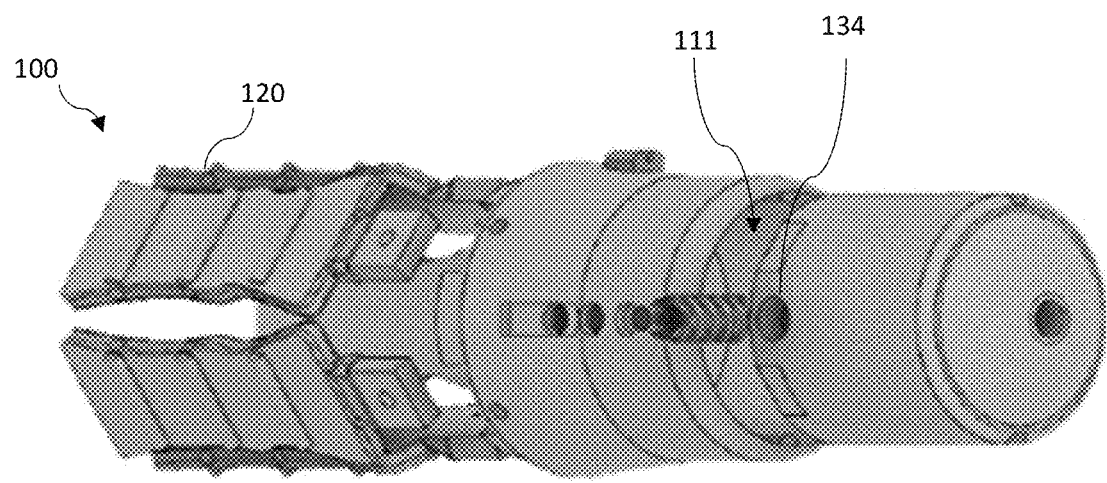
FIG. 2 is a schematic exploded perspective view of an exemplary embodiment of a prosthetic.
Figure 3:
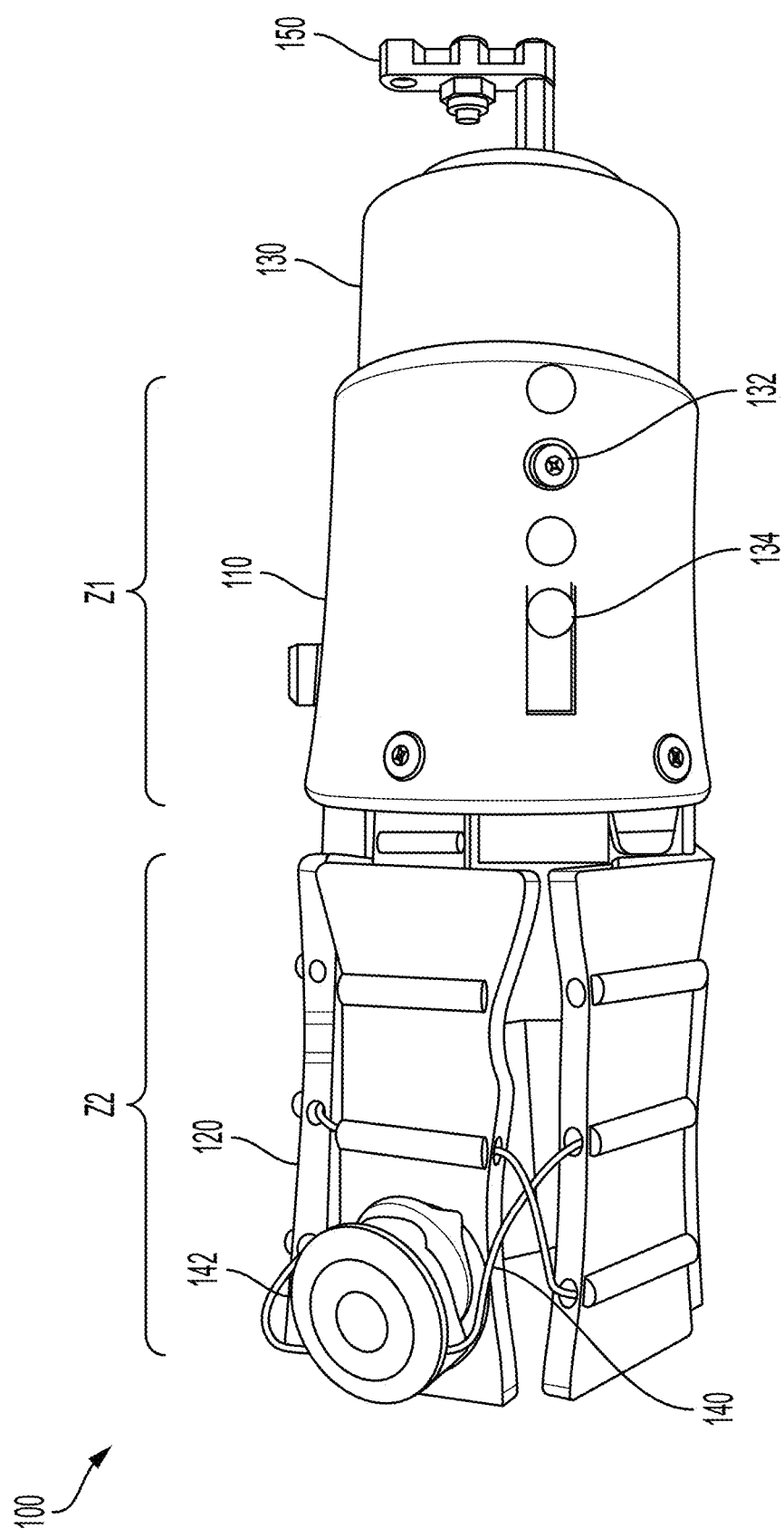
FIG. 3 is a side view of an exemplary embodiment of a prosthetic.

FIGS. 1-3 show exemplary embodiments of a prosthetic 100 for a limb extending distally to a limb end. The prosthetic 100 includes a main body 110 having an opening 111 for receiving the limb end and having a circumference. When the prosthetic 100 is fitted onto the limb, the main body 110 defines a first zone of coverage Z1 of the limb.

In exemplary embodiments, the prosthetic 100 further includes a plurality of struts 120 directly or indirectly coupled to the main body 110, and distributed along the circumference of the main body 110. Each strut 120 has a main longitudinal extent (along longitudinal axis L) that is essentially orthogonal to the circumference of the main body 110 and that extends away from the main body 110 to define a second zone of coverage Z2 of the limb that is adjacent to the first zone of coverage. The first zone of coverage Z1 is distal of the second zone of coverage Z2.

In exemplary embodiments, each strut 120 includes a plurality of transverse through-openings 122 configured to receive a lace 140. The transverse through-openings 122 extend tangentially to the second zone of coverage Z2. Each strut 120, which can function as a 3D-printed flexible pad, can conform to the shape of the residual limb and apply compression as the lace 140 is tightened.

In exemplary embodiments, the prosthetic 100 can be particularly suited for transradial or below-elbow amputees with a wide range of amputations. Transradial amputees are missing their wrist joint and often parts of their radial bone. Embodiments according to the present disclosure can enable users to execute activities of daily living (ADLs) with minimal assistance.

In exemplary embodiments, the strut 120 is an elongated structure that is essentially plate-like. The strut 120 can be fully flat one side, to facilitate fabrication by 3D-printing on a 3D printer bed. The strut 120 can have a transverse width along a transverse axis T that is wider at the through-openings 122 than at locations between the through-openings 122. This can significantly optimize comfort and stability for the residual limb. The strut 120 can be reinforced by rib portions 124 at each through-opening 122, to increase durability in view of increased mechanical stress at the lace location. When the prosthetic 100 is fitted onto the limb end, each through-opening 122 extends essentially tangentially to the circumference of the limb end.

In exemplary embodiments, the prosthetic 100 further includes one or more laces 140 threaded through the through-openings 122 of the plurality of struts 120, and a lacing closure system 142 configured for tightening the one or more laces 140. The lacing closure system 142 can be any suitable lacing closure system known in the art, such as, but not limited to, a dial lacing system.

The combination of the struts 120 and a lacing system including one or more laces 140 and a lacing closure system 142 can be particularly advantageous for circumference adjustment, as it can allow the prosthetic to adapt to the shape of the residual limb of a user, and can be uniformly compressed by the lace, to completely conform to the residual limb shape and create an anatomical compression hold on the limb while simultaneously providing space for air ventilation and padding. The prosthetic 100 can include any number of struts 120. In exemplary embodiments, more than 3 struts 120 is preferrable for sufficient limb support. In exemplary embodiments, 3-7 struts 120 are preferred to provide a balance between flexibility, component strength and ventilation. In an exemplary embodiment, 5 struts 120 are preferred. However, the prosthetic 100 can include fewer or more struts 120 without departing from the scope of the present disclosure.

In exemplary embodiments, the struts 120 can be 3D-printed. Alternatively, the struts 120 can be formed by injection molding, or any other suitable manufacturing processes known in the art. If the struts 120 are 3D-printed, an infill level of 30%-80% is preferred, more preferably 40%-60%, and even more preferably 50%, though lower and higher infill levels are acceptable without departing from the scope of the present disclosure.

The inventor has evaluated the relationship between strut infill levels and flexibility to determine suitable rigidity-to-flexibility combinations while maintaining the affordability of the print. The indicator of adequate flexibility to rigidity balance is the ability of the strut to maintain its shape after compression. Five struts of different infill levels, 30%, 40%, 50%, 60%, and 70%, were manually tested for bending and compression. Once the increase in infill surpassed 80%, the inventor found that it became difficult to compress the strut shape. Since an 80%-infilled strut infill may increase the cost by 12%, an infill level of 30%-80% is preferred, more preferably 40%-60%, and even more preferably 50%, was determined to be preferred as the medium range to ensure the strut was low-cost, structurally sound, and sufficiently flexible to provide user comfort.

In exemplary embodiments, the struts 120 can include polylactic acid (PLA), tough PLA, thermoplastic polyurethane (TPU), or any other suitable 3D-printable material known in the art. Generally, TPU or other flexible materials are preferrable for the struts 120. In some applications, tough PLA may be preferred, alone, or in combination with other materials, as it is a strong, durable 3D-printed material suitable for low-cost prosthetic sockets. PLA and tough PLA may be preferred for the main body 110 and/or areas supporting the struts 120 due to their relative rigidity.

In exemplary embodiments, when using TPU, 3D-printing parameters may be set such that the infill pattern is cross 3D, the shell thickness is 0.8 mm (walls) by 0.7 mm (roof), normal supports are enabled, and bed adhesion is enabled. For Tough PLA, 3D-printing parameters may be set such that the infill density is 20%, the infill pattern is triangles, the shell thickness is 0.8 mm (walls) by 1.2 mm (roof), normal supports are enabled, and bed adhesion is enabled.

In exemplary embodiments, the prosthetic 100 further includes a cap 130 having a concave portion configured to accommodate the limb end. An end of the cap 130 can be coupled, e.g., to a holding tool 150, such as a hook, or any other suitable attachment known in the art, including but not limited to powered (e.g., electric or body-powered), or non-powered prosthetic attachments. For example, in transradial prosthetic applications, the end of the cap 130 may be coupled to a myoelectric or body-powered hand control apparatus.

Figure 4:
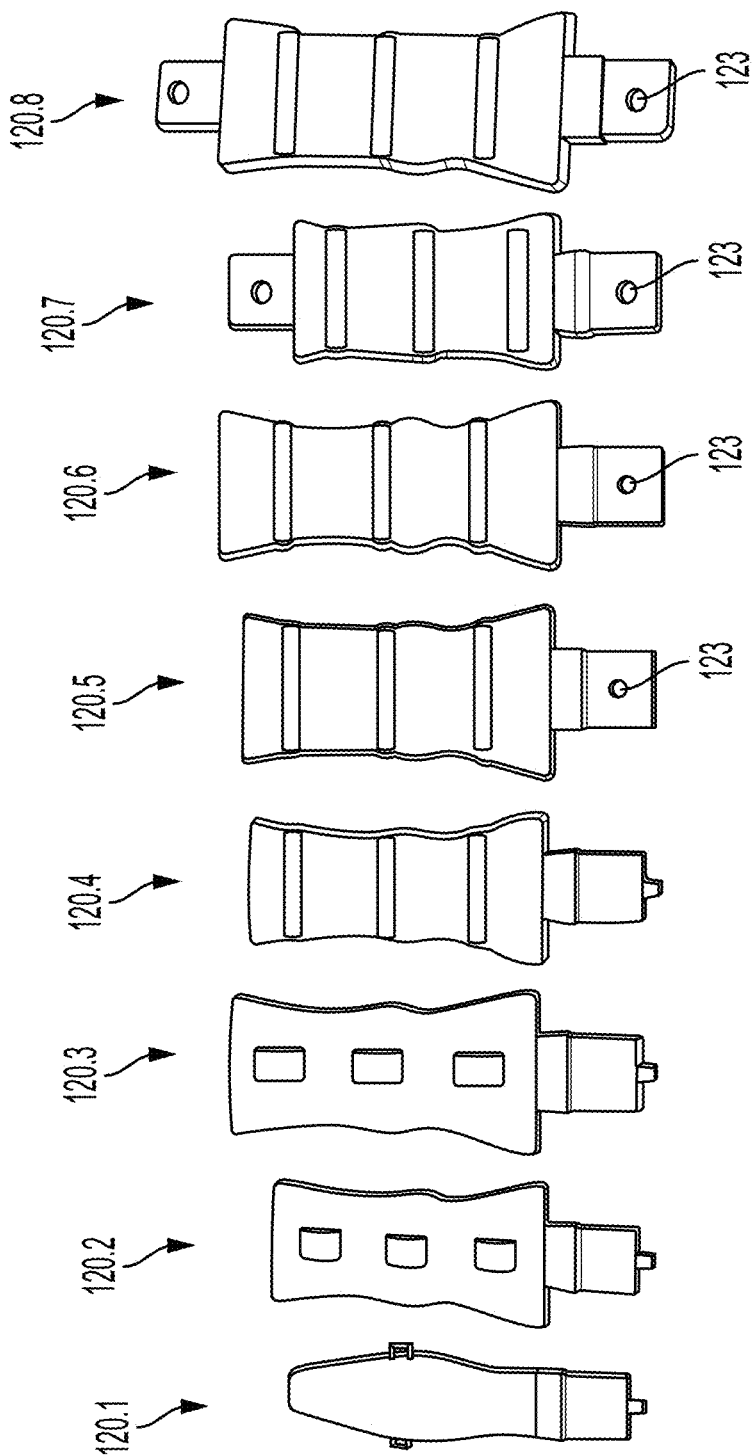
FIG. 4 shows eight exemplary embodiments of a strut for a prosthetic.

FIG. 4 shows eight exemplary embodiments 120.1-120.8 of a strut 120 for a prosthetic 100 developed during testing, which involved hundreds of iterations. The seventh and eighth exemplary embodiments 120.7, 120.8 are preferred, though the scope of the present disclosure is not limited to those embodiments. Although the following description specifies material and dimensional characteristics, the exemplary embodiments 120.1-120.8 of a strut 120 for a prosthetic 100 can be implemented using any suitable material and at any suitable scale, without departing from the scope of the present disclosure.

The first and second exemplary embodiments 120.1, 120.2 were made with PLA. Embodiment 120.2 includes three arches on a main surface of the strut 120, thus providing three through-openings 122 configured to receive a lace 140. The three through-openings 122 can provide an even distribution of pressure across the strut regions with a greater surface area, optimizing comfort and stability for the residual limb.

Furthermore, the areas around each through-opening 122, where the lacing closure system 142 applies pressure, feature an expanded width to enhance the strut's grip on the anatomical features of the limb.

The third exemplary embodiment 120.3 is a scaled version of the second exemplary embodiment 120.2, fabricated using TPU material. This embodiment also features click-in connections into the main body 110, along with arch-shaped through-openings 122 for the passage of the lace 140. A click-in connection can include a projection on one element (e.g., the strut 120 or the main body 110) and a receiving opening on another element (e.g., the main body 110 or the strut 120). In exemplary embodiments, a section of the projection can have an increased radius for a more secure connection and to provide auditory or sensory feedback during connection.

The fourth, fifth, sixth, seventh and eighth exemplary embodiments 120.4-120.8 differ from the first three 120.1-120.3 in advantageous ways, in view of modifications made after evaluating and receiving professional feedback. The exemplary embodiments 120.4-120.8 integrate the through-openings 122 directly into the structural composition of the strut 120 to reduce the risk of damage to the potentially weaker arch structure due to added compression. These embodiments also include an increased surface area in contact with the user's residual limb, and implement a more robust and secure method, such as screws or a locking mechanism, to affix the strut firmly within the main body 110. The exemplary embodiments 120.5-120.8 include a first hole 123 configured to allow the strut 120 to be secured into the main body 110 by a screw.

The sixth exemplary embodiment 120.6 is longer than the fifth 120.5, to accommodate longer amputations.

The seventh and eighth embodiments 120.7, 120.8 include a second hole 125 configured to connect to a cuff (e.g., an elbow cuff).

In exemplary embodiments, a lacing system can be particularly advantageous to adjust the compression and circumference of the prosthetic 100. A lacing system can be particularly advantageous, as it can provide evenly distributed pressure, adjustment to the size in both directions (compression and decompression), and easy adjustment with one hand. The inventor has found that a dial lacing system is particularly user-friendly for prosthetic applications, and can be attached to the prosthetic 100 at an attachment point. In exemplary embodiments, S2-Snap BOA Cartridge Dials® and M4 BOA® dials were tested. Other attachment mechanisms known in the art are suitable without departing from the scope of the present disclosure. For example, a ski boot clasp or a watch strap can be used to adjust the circumference of the prosthetic.

As shown in FIGS. 1-3, exemplary embodiments of a prosthetic 100 can include a spring lock mechanism for length adjustment, e.g., including a spring-activated pin 132 that locks into one of a plurality of corresponding holes 134 in a telescoping structure. This can provide a user-friendly and accessible solution for length adjustment. In operation, the user may press a button (e.g., the spring-activated pin 132 and pull one element of the telescoping structure from the other, upon which the spring-activated pin 132 will lock into the desired corresponding hole 134. This mechanism can also provide a universal fit device to attach and detach accessories (e.g., holding accessories) for the prosthetic 100. The prosthetic 100 can include, e.g., on the main body 110 or an adjacent structure, a spring-activated pin 132 corresponding to lock into a corresponding hole 134 in a prosthetic accessory. In exemplary embodiments, at least a portion of the main body 110 may taper to provide a more realistic arm shape, as shown, e.g., in FIGS. 1-3.

Figure 5:
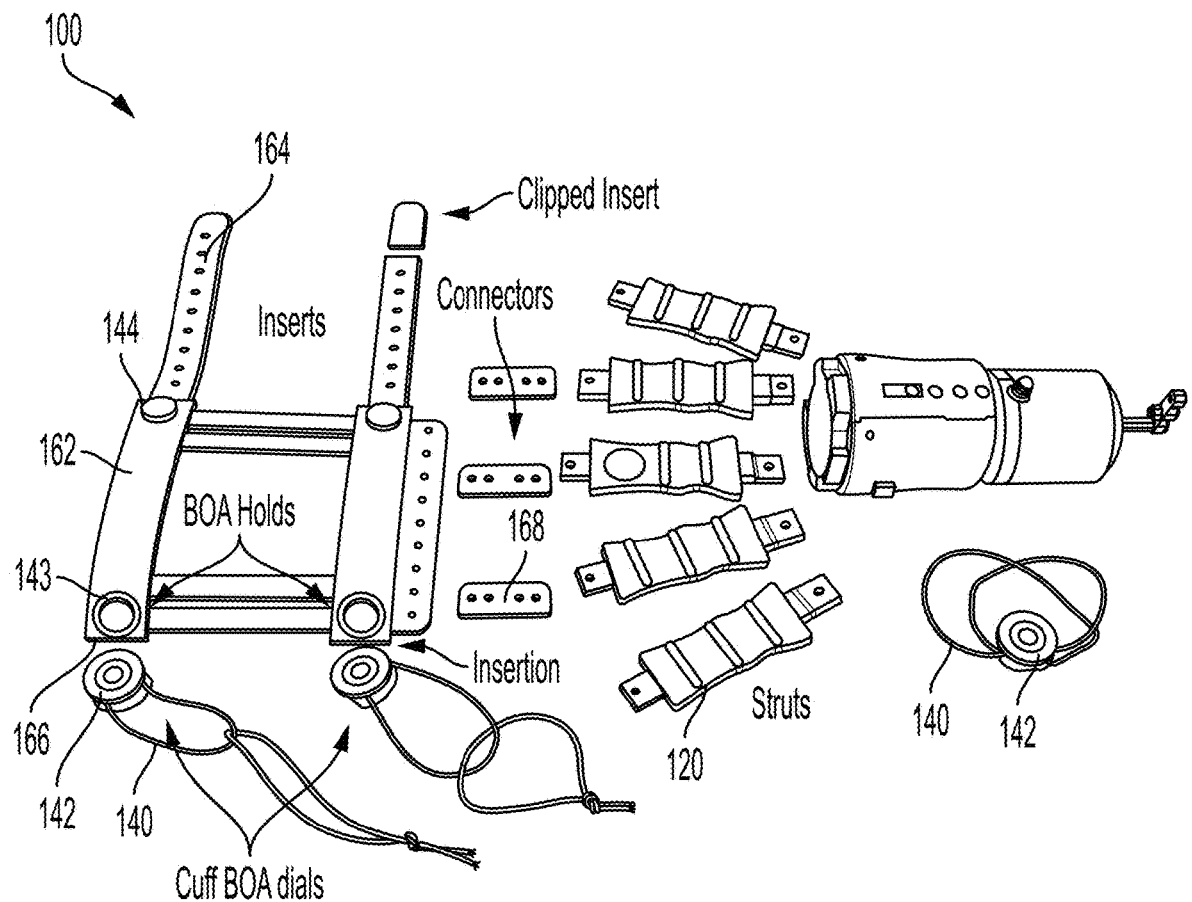
FIG. 5 is an exploded view of an exemplary embodiment of a prosthetic including a cuff.
Figure 6:
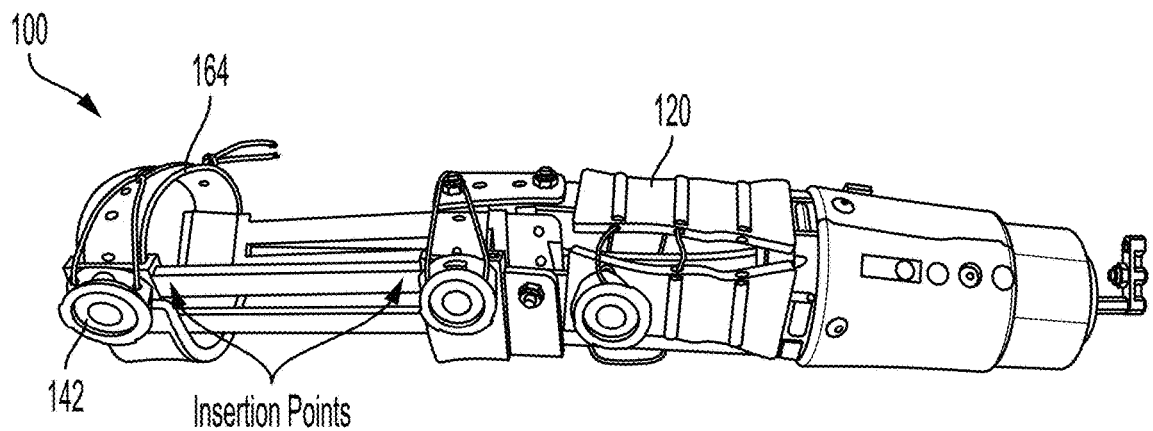
FIG. 6 is a side view of an exemplary embodiment of a prosthetic including a cuff.
Figure 7:
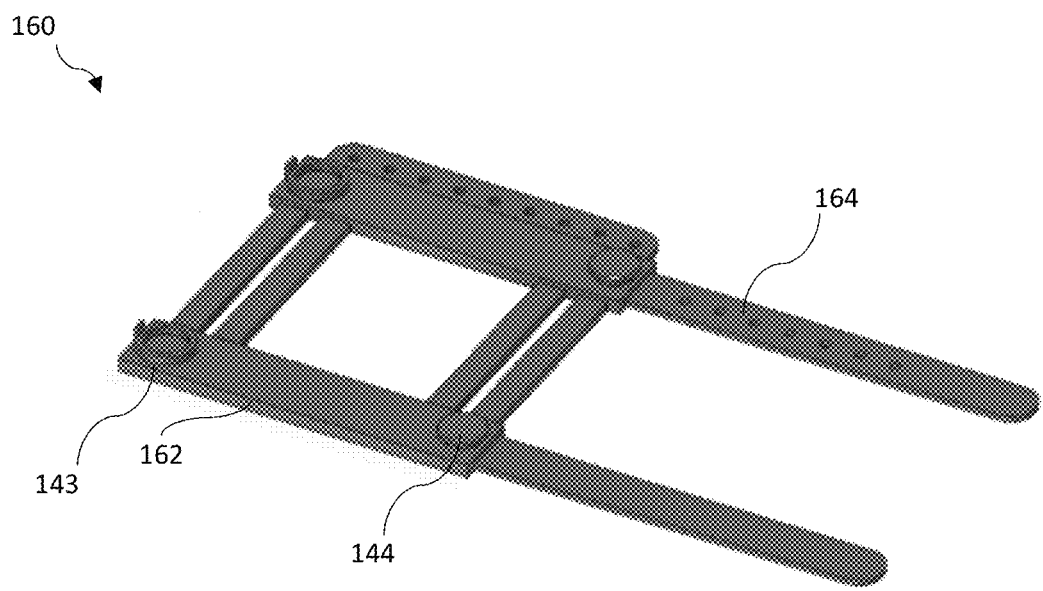
FIG. 7 is a schematic perspective view of an exemplary embodiment of a cuff.
Figure 8:
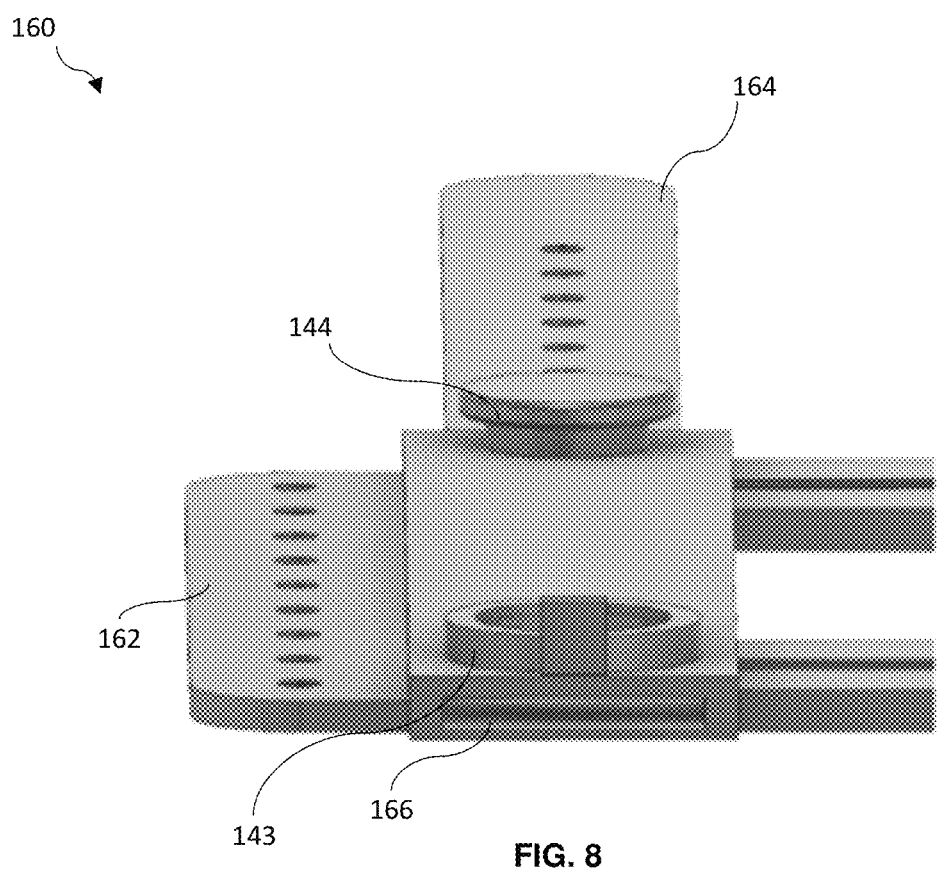
FIG. 8 is a schematic perspective view of a portion of an exemplary embodiment of a cuff.

FIGS. 5 and 6 show exemplary embodiments of a prosthetic 100 including a cuff 160, and FIGS. 7 and 8 show an exemplary cuff 160. One purpose of the cuff 160 is to increase the effectiveness of the prosthetic 100 by distributing weight over a larger portion of the limb. In the case of an elbow cuff 160, the cuff 160 can advantageously distribute the weight over the epicondyles and in several additional areas while also creating a better hold on the anatomical features of the limb. In exemplary embodiments, the cuff 160 compresses the limb inward from the right and left sides to press into residual limb bone structures, such as the lateral and medial epicondyles, creating a firm anatomical hold.

In exemplary embodiments, the cuff 160 comprises a cuff main body 162, one or more tabs 164 at one side of the cuff main body 162, and one or more corresponding insertion points 166 on an opposite side of the cuff main body 162. The tabs 164 are configured to flex and to be inserted into the corresponding insertion points 166 to form a circumference around a limb portion. Advantageously, the tabs 164 can be inserted into the insertion points 166 at a selectable depth, in order to accommodate various limb circumferences. Advantageously, the tabs 164 can be clipped to fit residual limbs with smaller circumferences.

In exemplary embodiments, the cuff 160 is configured to connect to the plurality of struts. For example, the cuff main body 162 is configured to directly connect to at least one of the plurality of struts 120, and one or more cuff attachment elements 168 are configured to directly connect to a tab 164 and to a strut 120. The attachment elements 168 can be plate-like for ease of printing. Cuff connections can include click-in connections, as previously described, or any other suitable connection mechanism. A side of the cuff main body 162, and one of the tabs 164, can include multiple openings to accommodate connections to the struts at various points along these elements, in order to accommodate various limb circumferences.

In exemplary embodiments, the cuff 160 includes a lace 140 and a lacing closure system 142 configured for tightening the cuff 160 around the limb. The lacing closure system 142 can be fitted onto an attachment point 143, e.g., on the cuff main body 162. During fitting, a lace 140 can loop around or otherwise be attached to a lace hold 144, e.g., also on the cuff main body 162, to tighten the cuff 160.

In exemplary embodiments, the cuff 160 includes an open space, e.g., between the one or more tabs 164, to create comfortability and facilitate a full range of motion, in view of, e.g., the anatomical fold of an elbow.

In exemplary embodiments, to assemble the cuff 160, a tab 164 is be belted over the residual limb and placed into the corresponding insertion point 166. A lacing closure system 142 is then placed and secured in the attachment point 143, and the lace 140 is wrapped around the limb and attached to the lace hold 144, to create compression on both sides of the limb.

The cuff 160 can be 3D-printed flat on a 3D printer bed. For example, the cuff main body 162 and the one or more tabs 164 each have a fully flat side configured such that the cuff main body 162 and the one or more tabs 164 are 3D-printed on a flat 3D printer bed. This can ensure printing ease, e.g. in TPU, though the cuff 160 can alternatively include PLA, tough PLA, or any other suitable 3D-printable material known in the art. Generally, TPU or other flexible materials are preferrable for the cuff 160. TPU may be particularly advantageous for the adaptable circumference mechanism of the cuff 160, as it has low shore hardness to allow the 3D-printed socket to conform to the shape of the limb. It is also sufficiently flexible to distribute forces around the residual limb, which can improve comfortability. TPU with high shore hardness can also be used.

Figure 10:
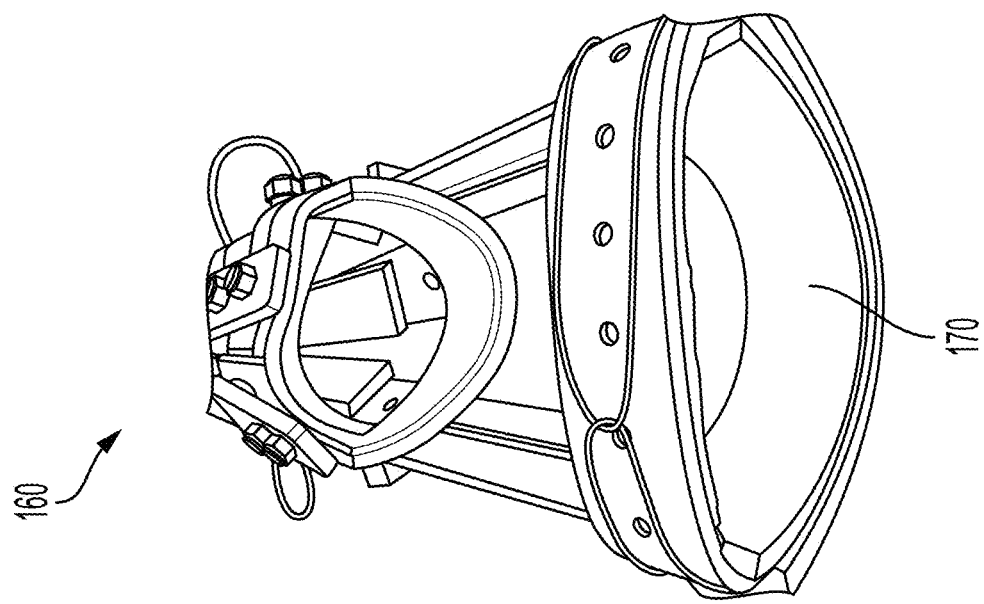
FIGS. 9 and 10 are perspective views of a portion of an exemplary embodiment of a cuff including a liner.
Figure 9:
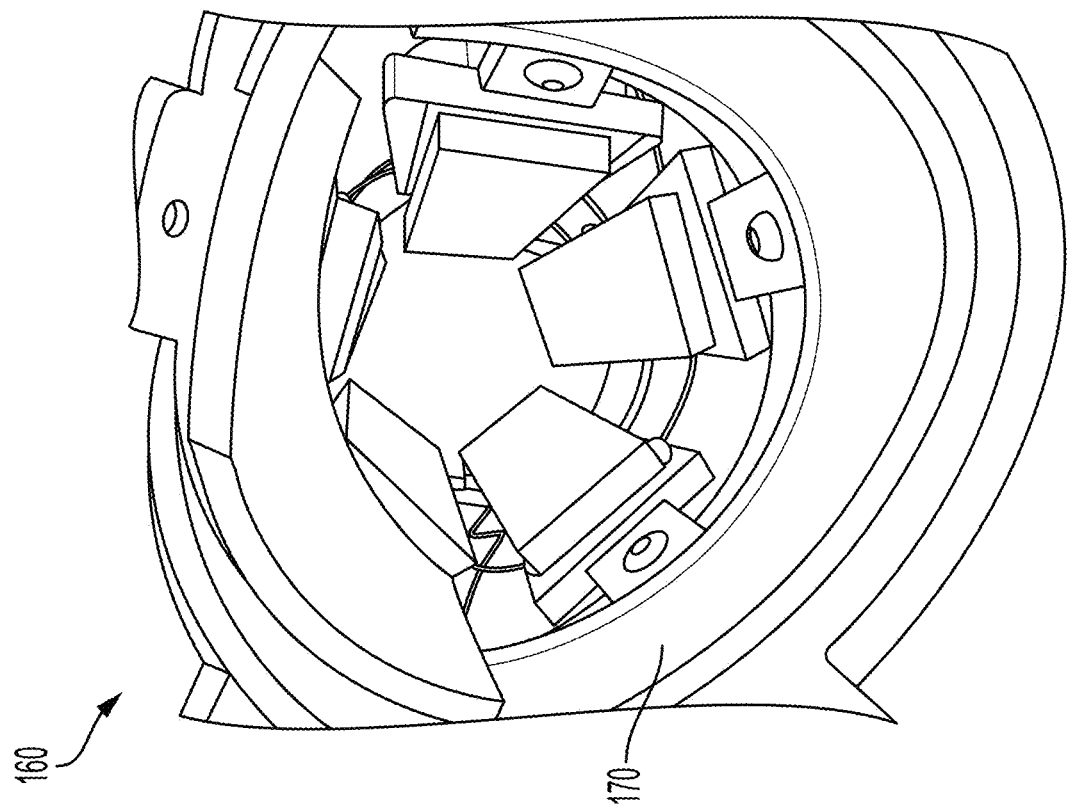

FIGS. 9 and 10 show an exemplary cuff 160 including a liner 170. A liner 170 can improve amputee safety and comfort by providing cushioning between the residual limb and the prosthetic socket. A liner 170 can also create friction between the prosthetic 100 and the residual limb, thus improving function. A liner 170 can include, but is not limited to, a skin-safe silicone liner, which can create a suitable hold between the residual limb and the prosthetic socket.

Figure 11:
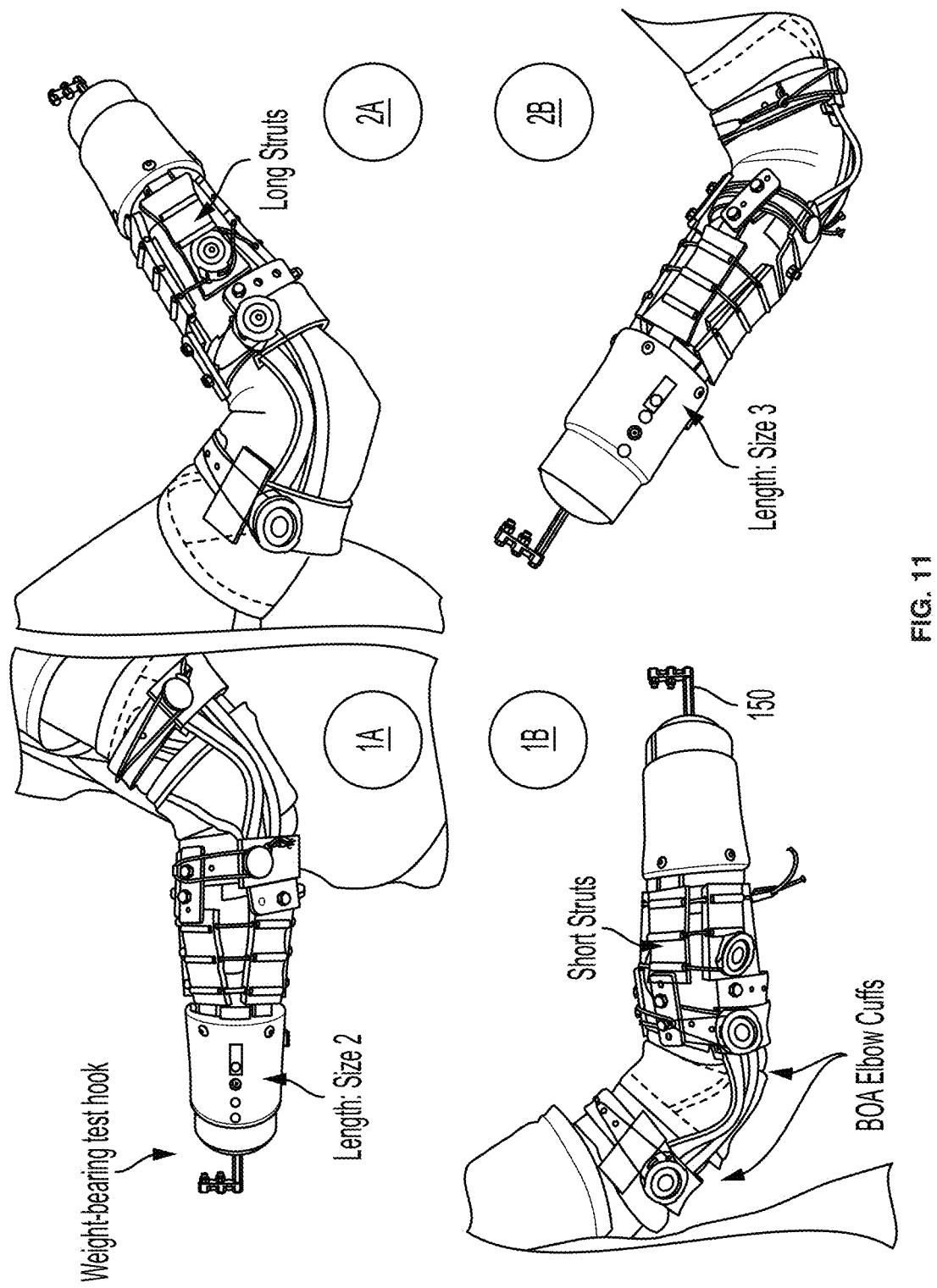
FIGS. 11 and 12 show various views of exemplary embodiments of a prosthetic during use.
Figure 12:
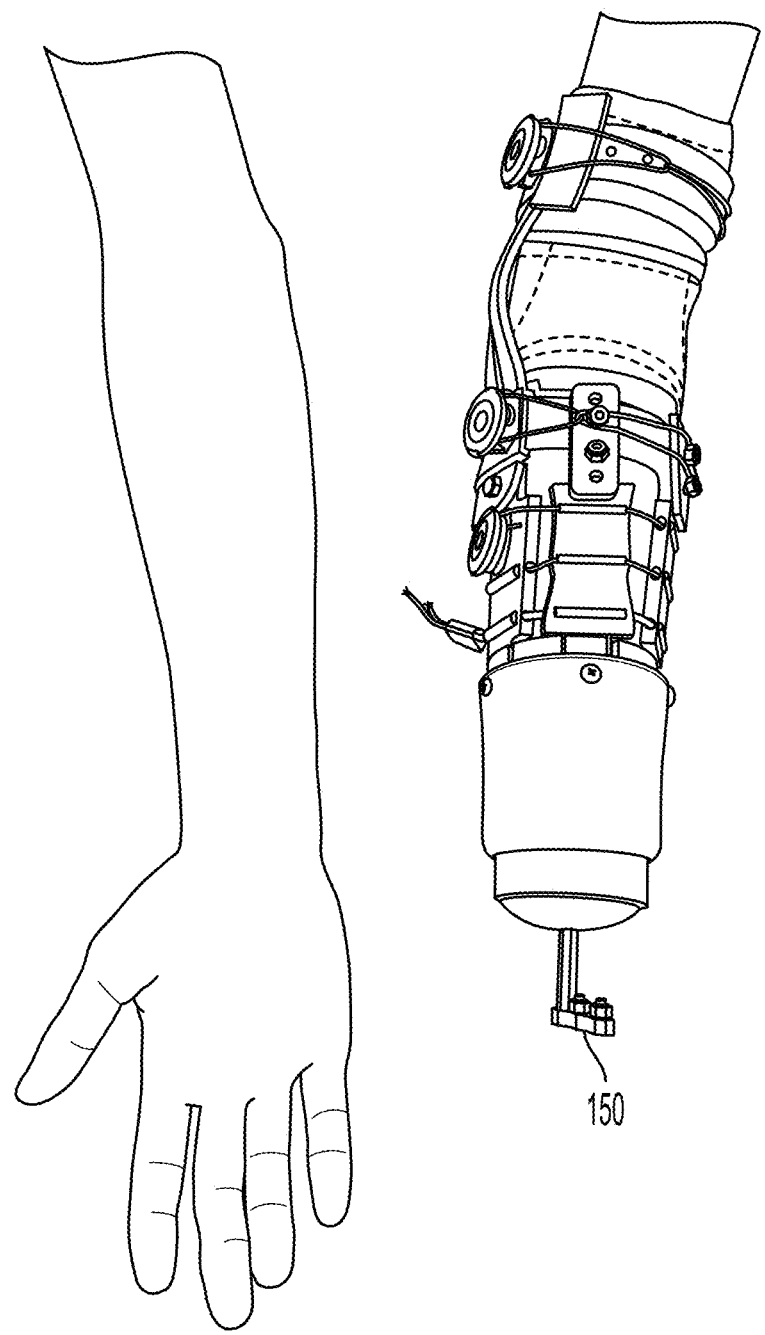

FIGS. 11 and 12 show exemplary prosthetics 100, fitted with a hook 150, during operation by a user.

Exemplary prosthetics 100 according to the present disclosure can provide secure attachment onto anatomical features above the elbow, below the elbow, and at the end of the amputated limb. During experimentation, the inventor found that prosthetics 100 according to the present disclosure were rated about 2 points higher (on a 1-10 scale) than each amputee's current socket. Additionally, exemplary prosthetics 100, e.g., combining a lacing system, a telescoping limb length adjust feature, and soft prosthetic straps around the residual limb, can accommodate various limb sizes, including, but not limited to, limb lengths between 10.5 cm and 19 cm and limb circumferences between 13.5 cm and 25 cm, while providing consistent compression throughout. Moreover, the prosthetics tested by the inventor passed most socket standards, supporting over 9 kg vertically and 6 kg horizontally, which are key benchmarks for a viable prosthetic, although these weight bearing characteristics are not limiting of the present disclosure.

Exemplary prosthetics 100 according to the present disclosure can provide low-cost, e.g., 3D-printed solutions in the form of a universal fit transradial prosthetic that can address the pressing need, particularly with amputees in developing countries, for an accessible and adjustable prosthetic that can drastically improve their lives. One potential price point for a prosthetic 100 may be as low as $40 or lower (i.e., two orders of magnitudes less than conventional systems), and can be distributed in the form of an easy-to-assemble kit that can be donned immediately without a healthcare professional, and which can adjust to the user's size changes over time.

Exemplary prosthetics 100 according to the present disclosure can provide an amputee with a universal-fit prosthetic kit that can immediately be usable. The prosthetic 100 can adjust to various sized circumferences and lengths and support high loads vertically and horizontally to simulate daily activities performed by the user. It is therefore particularly suitable for satisfying the unmet needs of amputees globally, including in developing countries.

EXEMPLARY EMBODIMENTS

Further aspects of the disclosure are provided below. Aspects of these exemplary embodiments are largely analogous to the exemplary embodiments, examples, etc. as described above, whereby reference is made to the above for a detailed description.

Item 1. A prosthetic (100) for a limb, the limb extending distally to a limb end, the prosthetic (100) comprising:
  a main body (110) having an opening for receiving the limb end, and having a circumference, wherein the main body (110) defines a first zone (Z1) of coverage of the limb; and
  a plurality of struts (120) coupled to the main body (110) and distributed along the circumference of the main body (110), wherein each strut (120) has a main longitudinal extent that is essentially orthogonal to the circumference of the main body (110) and that extends away from the main body (110) to define a second zone (Z2) of coverage of the limb that is adjacent to the first zone (Z1) of coverage,
  wherein each strut (120) includes a plurality of transverse through-openings (122) configured to receive a lace (140), the transverse through-openings (122) extending tangentially to the second zone (Z2) of coverage.

Item 2. The prosthetic (100) of item 1, wherein a transverse width of each strut (120) is wider at the through-openings (122) than at locations between the through-openings (122).

Item 3. The prosthetic (100) of items 1-2, further comprising one or more laces (140) threaded through the through-openings (122) of the plurality of struts (120).

Item 4. The prosthetic (100) of items 1-3, further comprising a lacing closure system (142) configured for tightening the one or more laces (140).

Item 5. The prosthetic (100) of item 4, wherein the lacing closure system (142) is a dial lacing system.

Item 6. The prosthetic (100) of items 1-5, further comprising a cap (130) having a concave portion configured to accommodate the limb end.

Item 7. The prosthetic (100) of items 1-6, wherein the plurality of struts (120) include at least three struts (120).

Item 8. The prosthetic (100) of items 1-7, wherein the plurality of struts (120) include five struts (120).

Item 9. The prosthetic (100) of items 1-8, wherein the plurality of struts (120) are 3D-printed.

Item 10. The prosthetic (100) of items 1-9, wherein each strut (120) has a fully flat side configured such that the strut (120) is 3D-printed on a flat 3D printer bed.

Item 11. The prosthetic (100) of items 1-10, further comprising a cuff comprising:
  a cuff main body (162);
  one or more tabs (164) at one side of the cuff main body (162); and
  one or more corresponding insertion points (166) on an opposite side of the cuff main body (162), wherein the one or more tabs (164) are configured to flex and to be inserted into the one or more corresponding insertion points (166) to form a circumference around a limb portion.

Item 12. The prosthetic (100) of item 11, wherein the cuff is configured to connect to the plurality of struts (120).

Item 13. The prosthetic (100) of items 11-12, wherein the cuff main body (162) is configured to directly connect to at least one of the plurality of struts (120).

Item 14. The prosthetic (100) of items 11-13, further comprising cuff attachment elements (168) configured to directly connect to one of the one or more tabs (164) and to at least one of the plurality of struts (120).

Item 15. The prosthetic (100) of items 11-14, wherein the cuff main body (162) is lined with a silicone liner.

Item 16. The prosthetic (100) of items 11-15, further comprising a lace (140) for tightening the cuff around a limb.

Item 17. The prosthetic (100) of items 11-16, wherein the cuff main body (162) and the one or more tabs (164) are 3D-printed.

Item 18. The prosthetic (100) of items 11-17, wherein the cuff main body (162) and the one or more tabs (164) each have a fully flat side configured such that the cuff main body (162) and the one or more tabs (164) are 3D-printed on a flat 3D printer bed.

Item 19. A method of making the prosthetic (100) of items 1-18, comprising: 3D-printing the plurality of struts (120).

Item 20. A method of making the prosthetic (100) of items 11-18, comprising: 3D-printing the cuff main body (162) and the one or more tabs (164).

It will be appreciated by those skilled in the art that the disclosure herein can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A prosthetic for a limb, the limb extending distally to a limb end, the prosthetic comprising:
  a main body having an opening for receiving the limb end, and having a circumference, wherein the main body defines a first zone of coverage of the limb; and a plurality of struts coupled to the main body and distributed along the circumference of the main body, wherein each strut has a main longitudinal extent that is essentially orthogonal to the circumference of the main body and that extends away from the main body to define a second zone of coverage of the limb that is adjacent to the first zone of coverage, wherein each strut includes a plurality of transverse through-openings configured to receive a lace, the transverse through-openings extending around the second zone of coverage, wherein the prosthetic further comprises a cuff including:
a cuff main body;
one or more tabs at one side of the cuff main body; and
one or more corresponding insertion points on an opposite side of the cuff main body, wherein the one or more tabs are configured to flex and to be inserted into the one or more corresponding insertion points to form a circumference around a limb portion.

2. The prosthetic of claim 1, wherein a transverse width of each strut is wider at the through-openings than at locations between the through-openings.

3. The prosthetic of claim 1, further comprising one or more laces threaded through the through-openings of the plurality of struts.

4. The prosthetic of claim 1, further comprising a lacing closure system configured for tightening the one or more laces.

5. The prosthetic of claim 4, wherein the lacing closure system is a dial lacing system.

6. The prosthetic of claim 1, further comprising a cap having a concave portion configured to accommodate the limb end.

7. The prosthetic of claim 1, wherein the plurality of struts include at least three struts.

8. The prosthetic of claim 1, wherein the plurality of struts include five struts.

9. The prosthetic of claim 1, wherein the plurality of struts are 3D-printed.

10. The prosthetic of claim 9, wherein each strut has a fully flat side configured such that the strut is 3D-printed on a flat 3D printer bed.

11. The prosthetic of claim 1, wherein the cuff is configured to connect to the plurality of struts.

12. The prosthetic of claim 1, wherein the cuff main body is configured to directly connect to at least one of the plurality of struts.

13. The prosthetic of claim 1, further comprising cuff attachment elements configured to directly connect to one of the one or more tabs and to at least one of the plurality of struts.

14. The prosthetic of claim 1, wherein the cuff main body is lined with a silicone liner.

15. The prosthetic of claim 1, further comprising a lace for tightening the cuff around a limb.

16. The prosthetic of claim 1, wherein the cuff main body and the one or more tabs are 3D-printed.

17. The prosthetic of claim 16, wherein the cuff main body and the one or more tabs each have a fully flat side configured such that the cuff main body and the one or more tabs are 3D-printed on a flat 3D printer bed.

18. A method of making the prosthetic of claim 1, comprising:
3D-printing the plurality of struts.

19. A method of making the prosthetic of claim 1, comprising:
3D-printing the cuff main body and the one or more tabs.

* * * * *